(12) United States Patent
Valentino

(10) Patent No.: US 9,168,177 B2
(45) Date of Patent: Oct. 27, 2015

(54) SLIP-OVER LIGHT BLOCKING SLEEP MASK

(76) Inventor: Alexander Valentino, Sicklerville, NJ (US)

(*) Notice: Subject to any disclaimer, the term of this patent is extended or adjusted under 35 U.S.C. 154(b) by 441 days.

(21) Appl. No.: 13/477,302

(22) Filed: May 22, 2012

(65) Prior Publication Data

US 2013/0117899 A1    May 16, 2013

Related U.S. Application Data

(60) Provisional application No. 61/559,146, filed on Nov. 14, 2011.

(51) Int. Cl.
*A42B 1/04*    (2006.01)
*A61F 9/04*    (2006.01)

(52) U.S. Cl.
CPC ........................................ *A61F 9/04* (2013.01)

(58) Field of Classification Search
CPC ............ A41D 20/00; A42B 1/06; A42B 1/24; A42B 1/247; A61F 9/04
USPC ............................ 2/171, 209.11, 209.3, 209.7
See application file for complete search history.

(56) References Cited

U.S. PATENT DOCUMENTS

| | | | | |
|---|---|---|---|---|
| 4,520,510 A | * | 6/1985 | Daigle | .............................. 2/452 |
| 4,712,254 A | * | 12/1987 | Daigle | ................... A41D 20/00 2/171 |
| 5,129,106 A | * | 7/1992 | Liou | ..................... A41D 20/00 2/411 |
| 6,115,843 A | * | 9/2000 | Travalgia | ......................... 2/171 |

* cited by examiner

*Primary Examiner* — Clinton T Ostrup
*Assistant Examiner* — Sally Haden
(74) *Attorney, Agent, or Firm* — Norman E. Lehrer

(57) ABSTRACT

This invention describes a slip-over sleep mask, having a tubular-shaped body consisting of a soft cloth or fabric material, which is to be used to effectively block out any light from entering a person's eyes while sleeping. The sleep mask is to be slipped over and worn around a person's head, as one piece, covering the eyes and ears. Permanently attached to the inside lower frontal portion of said tubular-shaped body is a separate ruffled or pleated piece of soft cloth or fabric material. This attached material fills in any gaps of space that exist in the areas between the eyes and nose of a person's face which would otherwise allow for any unwanted light to enter inward. The one piece, slip-over design of the sleep mask stretches and clings naturally to a person's face, thus preventing any movement or shifting of itself during sleep.

3 Claims, 8 Drawing Sheets

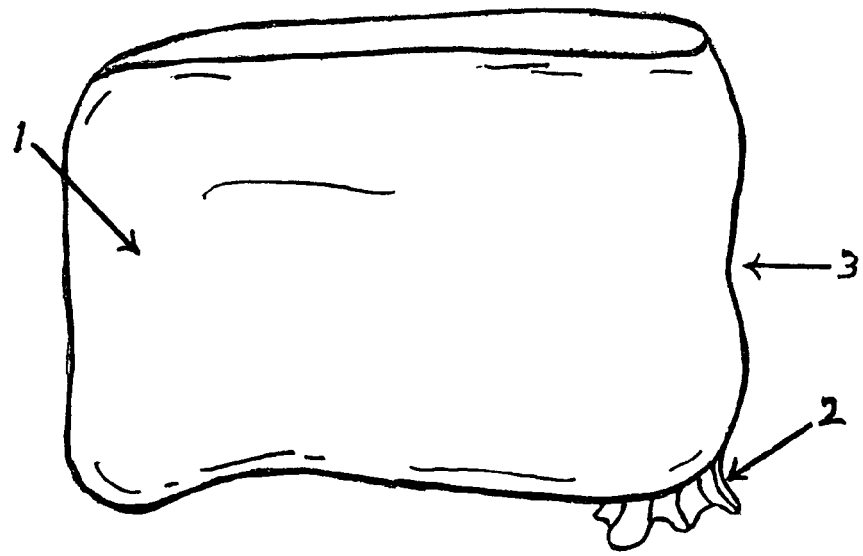

SLIP-OVER LIGHT BLOCKING SLEEP MASK

CROSS-REFERENCE TO RELATED APPLICATIONS

Related U.S. Application Data

Based upon earlier filed provisional application No. 61/559,146, filed on Nov. 14, 2011

REFERENCES CITED

U.S. PATENT DOCUMENTS

| | | |
|---|---|---|
| 6,363,285 B1 | January 2000 | Wey |
| D465,234 S | August 2000 | Gordon |
| D489,749 S | April 2000 | Landvik |
| D302,167 | August 1986 | Sherman |

BACKGROUND

1. Field of Invention

The present invention is directed toward a slip-over sleep mask, having a tubular-shaped body consisting of a soft cloth or fabric material, which is to be used to effectively block out any light from entering a person's eyes while sleeping. The sleep mask is to be slipped over and worn around a person's head, as one piece, covering the eyes, ears, top portions of the nose, as well as portions of the sides and back of the head. Permanently attached to the inside lower frontal portion of said tubular-shaped body is a separate ruffled or pleated piece, or pieces, of soft cloth or fabric material. This attached material, due to its design and location on the mask, fills in any gaps of space that exist in the lower areas between the eyes and nose of a person's face, thus creating a blockage to light. Without this said attached material, the mask would otherwise allow for any unwanted rays of light to enter inward into a person's field of vision through the said lower areas between the eyes and nose. These are areas that other sleep masks, presently available on the market today, fail to completely fill in and block from the light. The one piece, slip-over design, of the sleep mask of the present invention, enables the body of the mask to stretch and cling naturally and comfortably to a person's face and head, thus preventing any movement or shifting of itself during sleep. This same one piece design also eliminates the need for the use of any noisy, uncomfortable straps or bulky connectors that are presently used with other sleep masks marketed today. These straps and connectors are usually located at the sides or back of the head and could cause discomfort to a person while trying to sleep, especially during the normal movements of that person's head against a mattress or pillow. Related sleep aids that are currently marketed today utilize the above mentioned fastening methods, involving the noisy, uncomfortable straps or bulky attachments, to affix the sleep aid to the head. These straps and attachments have a tendency to break or come apart.

An additional result achieved by the use of the present invention is the containing and controlling of a person's hair while sleeping. If the hair on a person's head is too frizzy, unruly or in a state of experiencing too much volume, the natural stretch and cling fit of the sleep mask of the present invention helps to lightly compress the hair, keeping it in a more conformed and organized shape.

There is also a third result achieved by the use of the present invention. Since the ears of a person are also covered while wearing the slip-over sleep mask of the present invention, any surrounding noise levels that could disrupt a person's sleep are reduced.

2. Description of Prior Art

There are two other products available today that may seem similar in design, to the above mentioned present invention, but differ in overall construction and in problems that they set out to solve. One such invention is the Therapeutic Sleeping Aid Device (U.S. Pat. No. 6,363,285). This invention can be worn over the head in the form of a wrap but includes a far infrared radiation material which permeates into the skin of a human being. Another such invention is the Sound Muffling Sleep Mask (U.S. Pat. No. D465,234). This is a mask that does not consist of a one-piece, slip-over tubular design but rather is separated, having two separate ends that are to be connected at the back of the head, forming a large-layered lump where the connection is made. Both these inventions do not include a permanently attached ruffled or pleated piece of soft cloth or fabric material which is located in the inside lower frontal portion of its main body that fills in any gaps of space that exist in the areas between the eyes and nose of a person's face which would otherwise allow for any unwanted light to enter inward. In years past, there have been numerous types of sleep masks on the market that consisted of two ends that had to be connected to a person's head by means of stapled rubber straps, cloth straps, Velcro, and clips. These commonly seen masks may have contained added pieces of cloth or fabric material attached to their lower frontal portion, where the eyes and nose areas met, but so far, there has never been a one-piece, slip-over mask, that covered the eyes and ears, with a permanently affixed piece of ruffled or pleated cloth or fabric material attached on the inside frontal portion of the mask, where the eyes and nose areas of the mask meet.

SUMMARY OF THE INVENTION

The present invention is designed to overcome the deficiencies of any of the prior art mentioned above. An object of the present invention is to provide a one piece, slip-over sleep mask that completely blocks out any unwanted light from entering a person's field of vision. This sleep mask is comprised of a tubular-shaped body which consists of a soft cloth or fabric material and is to be slipped over and worn around a person's head, as one piece, covering the eyes and ears. Permanently attached to the inside lower frontal portion of said tubular-shaped body is a separate ruffled or pleated piece, or pieces, of soft cloth or fabric material. This attached material fills in any gaps of space that exist in the areas between the eyes and nose of a person's face which would otherwise allow for any unwanted light to enter inward. The one piece, slip-over design of the sleep mask stretches and clings naturally to a person's face and head, thus preventing any movement or shifting of itself during sleep.

Two additional results are achieved by the use of the present invention. One is the containing and controlling of a person's hair while sleeping. The natural stretch and cling fit of the sleep mask of the present invention helps to lightly compress the hair on a person's head, thus keeping it in a more conformed and organized shape. The other result achieved is the reduction of any surrounding noise levels that could disturb or disrupt a person's sleep. The slip-over mask of the present invention, while being worn, covers the ears of a person which in turn helps to block out sound.

BRIEF DESCRIPTION OF THE DRAWINGS

For illustration purposes, one presently preferred form of the invention is shown in the accompanying drawings; it

FIG. 4 is a left side view of the slip-over sleep mask of the present invention;

FIG. 5 is a right side view of the slip-over sleep mask of the present invention;

DETAILED DESCRIPTION OF THE PREFERRED EMBODIMENT

Figure 1:
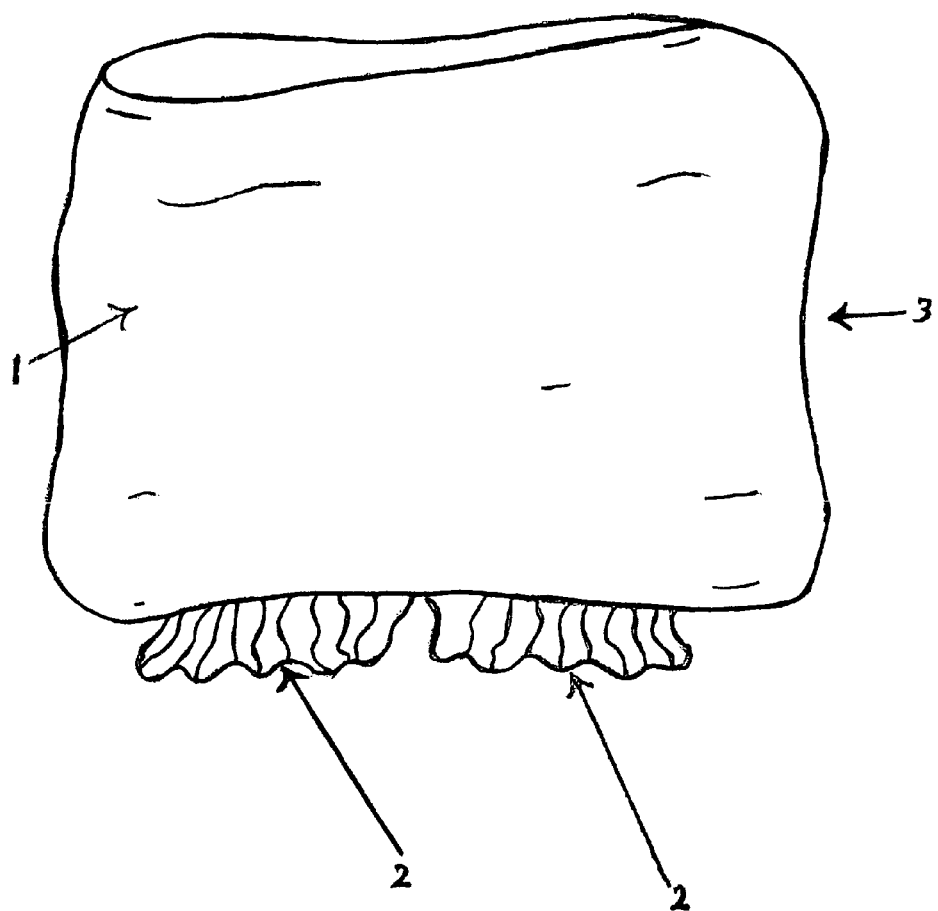
FIG. 1 is a front view of the slip-over sleep mask of the present invention.
Figure 2:
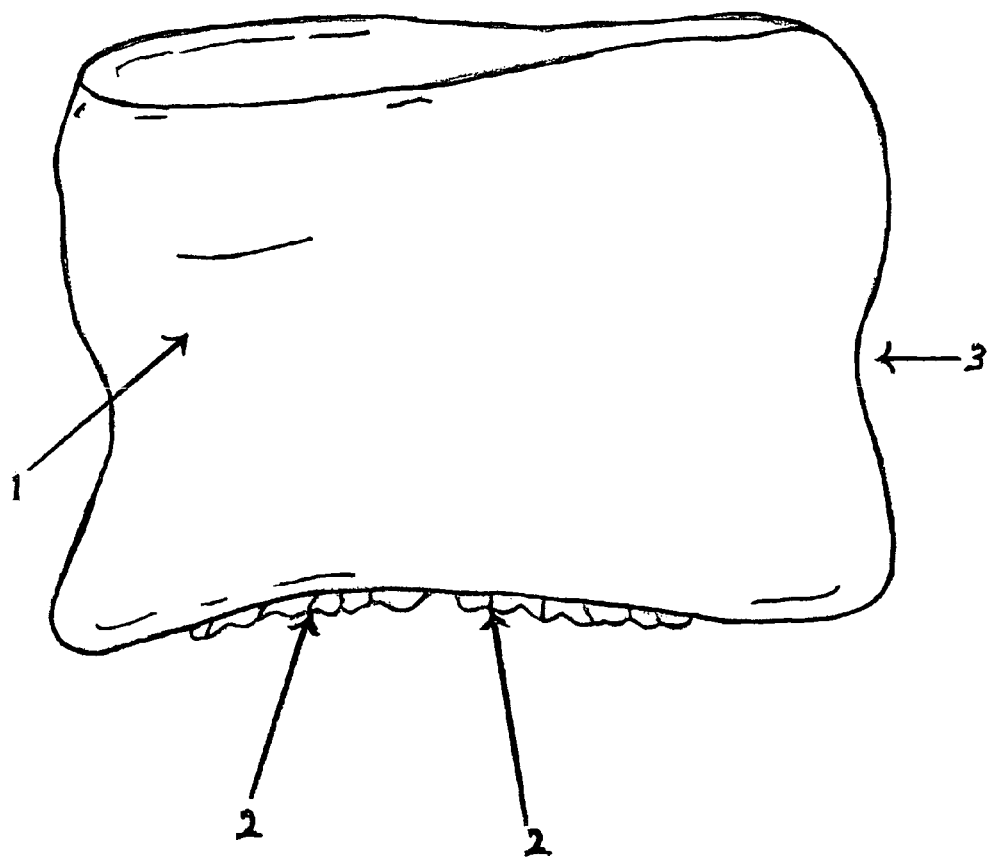
FIG. 2 is a rear view of the slip-over sleep mask of the present invention.

Now referring to the accompanying drawings in detail wherein like reference numerals have been used throughout the various figures to designate like elements, there is shown in FIGS. 1-10 a slip-over sleep mask constructed in accordance with the principles of the present invention and designated generally as 3.

The present invention 3 essentially is comprised of a tubular-shaped body 1 which consists of a soft, flexible cloth or fabric material. (See FIGS. 1-10.) This said tubular-shaped body 1 is to be slipped over and worn around a person's head, as one piece, covering the eyes, ears, top portion of the nose, as well as portions of the sides and back of the head. (See FIGS. 8-10.)

Figure 3:
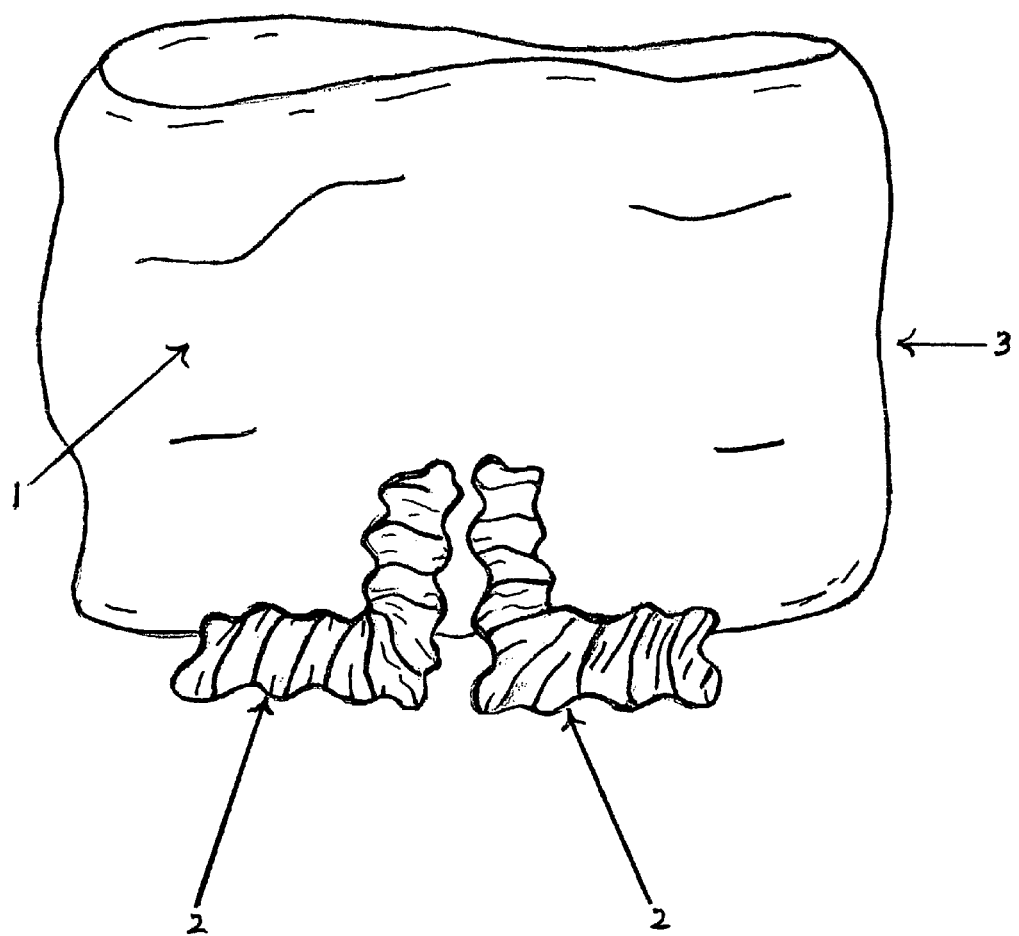
FIG. 3 is an inside front view of the slip-over sleep mask of the present invention whereby the tubular-shaped body of the present invention is turned inside out.
Figure 6:
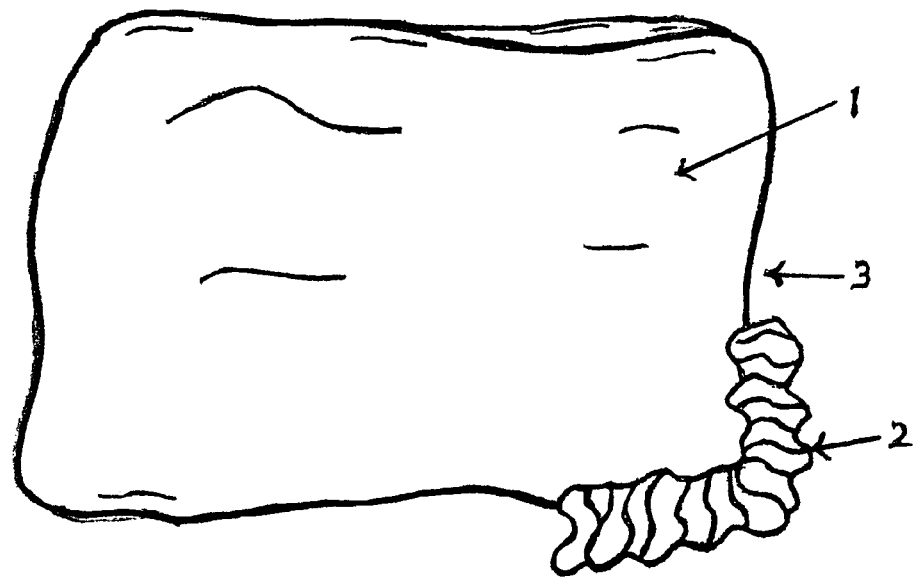
FIG. 6 is an inside right side view of the slip-over sleep mask of the present invention whereby the tubular-shaped body of the present invention is turned inside out.
Figure 7:
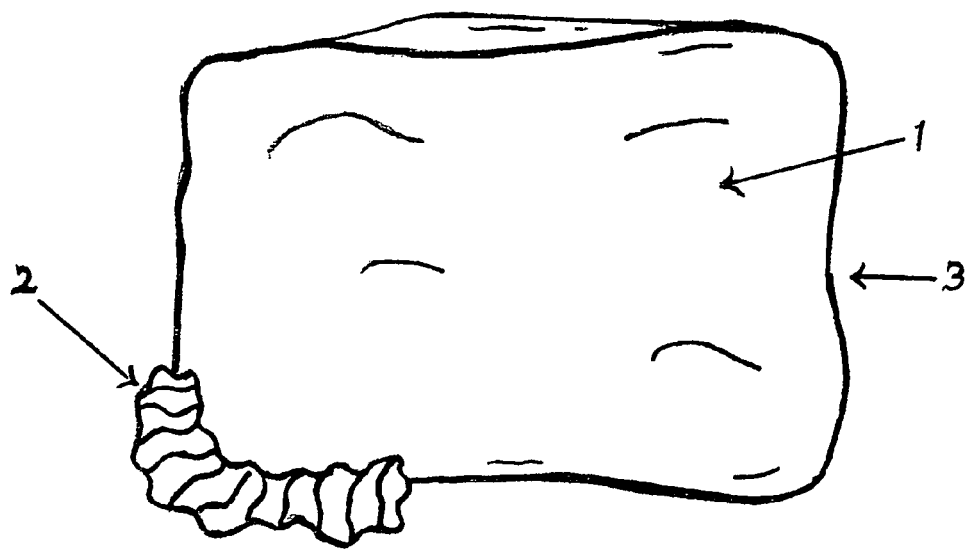
FIG. 7 is an inside left side view of the slip-over sleep mask of the present invention whereby the tubular-shaped body of the present invention is turned inside
Figure 8:
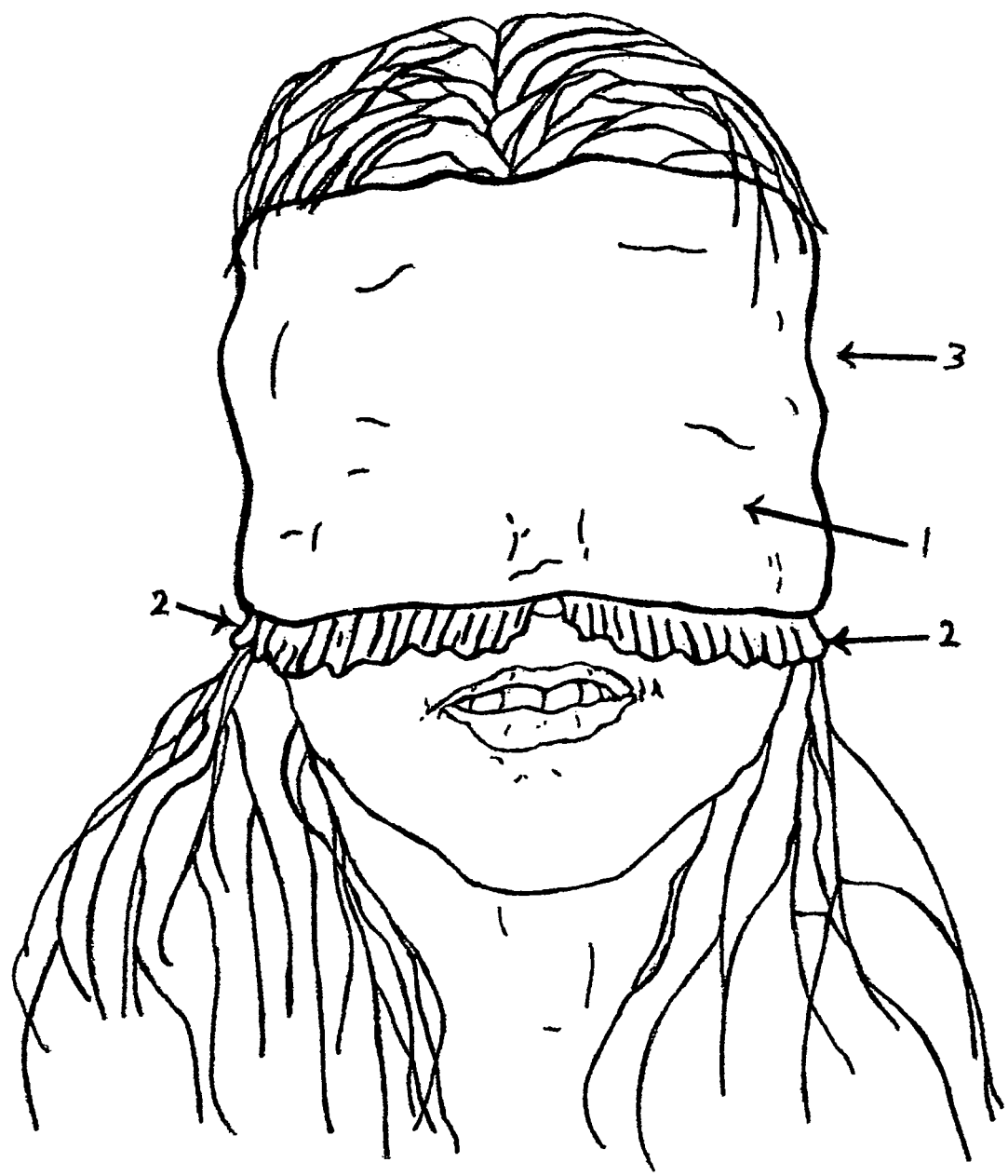
FIG. 8 illustrates a front view of a person wearing the slip-over sleep mask of the present invention.
Figure 9:
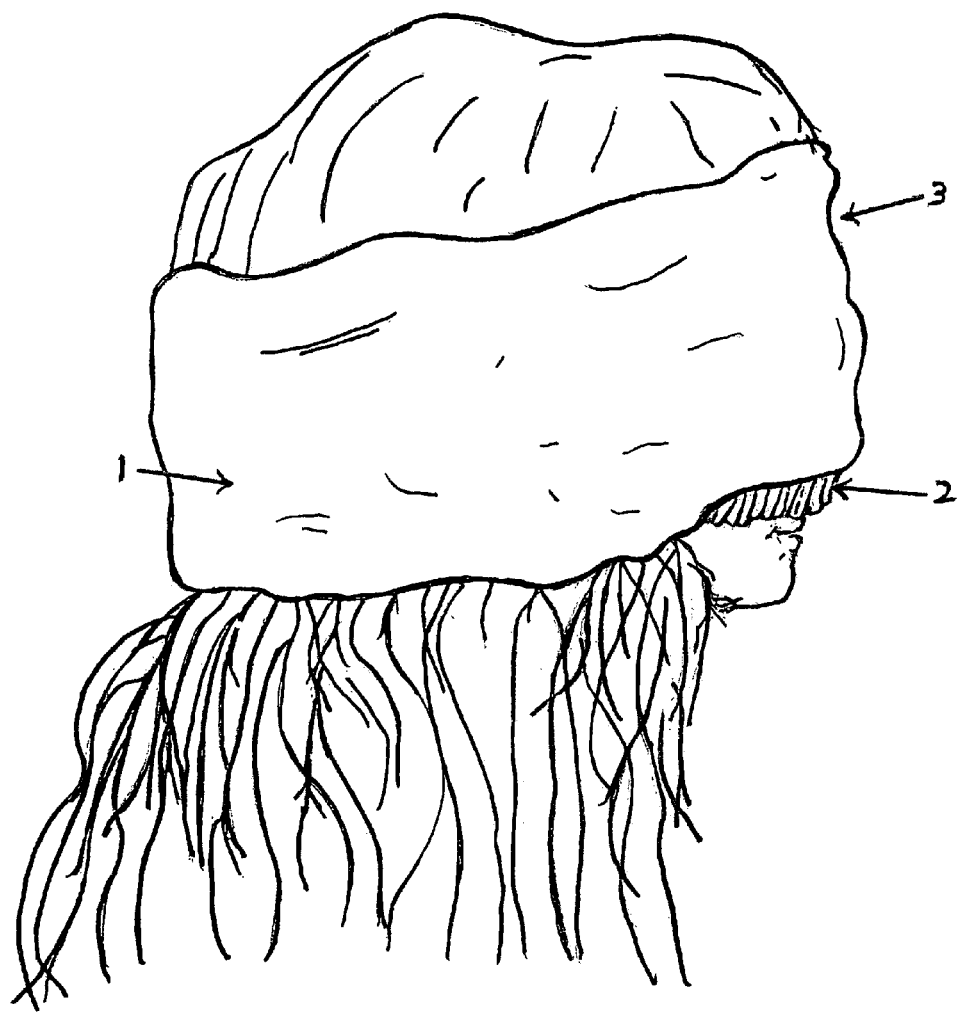
FIG. 9 illustrates a side view of a person wearing the slip-over sleep mask of the present invention.

Permanently attached to the inside lower frontal portion of said tubular-shaped body 1 is a separate ruffled or pleated piece, or pieces, of a soft cloth or fabric material 2 as shown in FIGS. 1-9. A full view of the said attached ruffled or pleated material 2 is illustrated in FIG. 3, where the entire tubular-shaped body 1, of the present invention 3, is shown turned inside out. The ruffled or pleated material 2 comprises a vertical section and a horizontal section, and said vertical section and said horizontal section are substantially perpendicular to one another and wherein said first and second pieces of material oppose one another. A lower portion of said attached ruffled or pleated material 2 material extends downward from its fixed inside position and protrudes through to the outside lower frontal portion of said tubular-shaped body 1, as shown in FIGS. 8-9, thus filling in any gaps of space that exist in the areas between the eyes and nose of a person's face which would otherwise allow unwanted rays of light to enter inward into a person's field of vision while the sleep mask of the present invention 3 is being worn. In FIG. 1, the lower edge of the frontal view of the attached ruffled or pleated material 2 can be seen protruding through to the outside lower frontal portion of the tubular-shaped body 1. The lower edge of the rear view of the attached ruffled or pleated material 2 protruding through to the outside lower frontal portion of the tubular-shaped body 1 can be seen in FIG. 2. The left outside lower edge of the attached ruffled or pleated material 2 can be seen in FIG. 4 protruding from the bottom of the tubular-shaped body 1. The right outside lower edge of the attached ruffled or pleated material 2 can be seen in FIG. 5 protruding from the bottom of the tubular-shaped body 1. A right inside view of the attached ruffled or pleated material 2 can be seen in FIG. 6, and a left inside view of the attached ruffled or pleated material 2 can be seen in FIG. 7.

Figure 10:
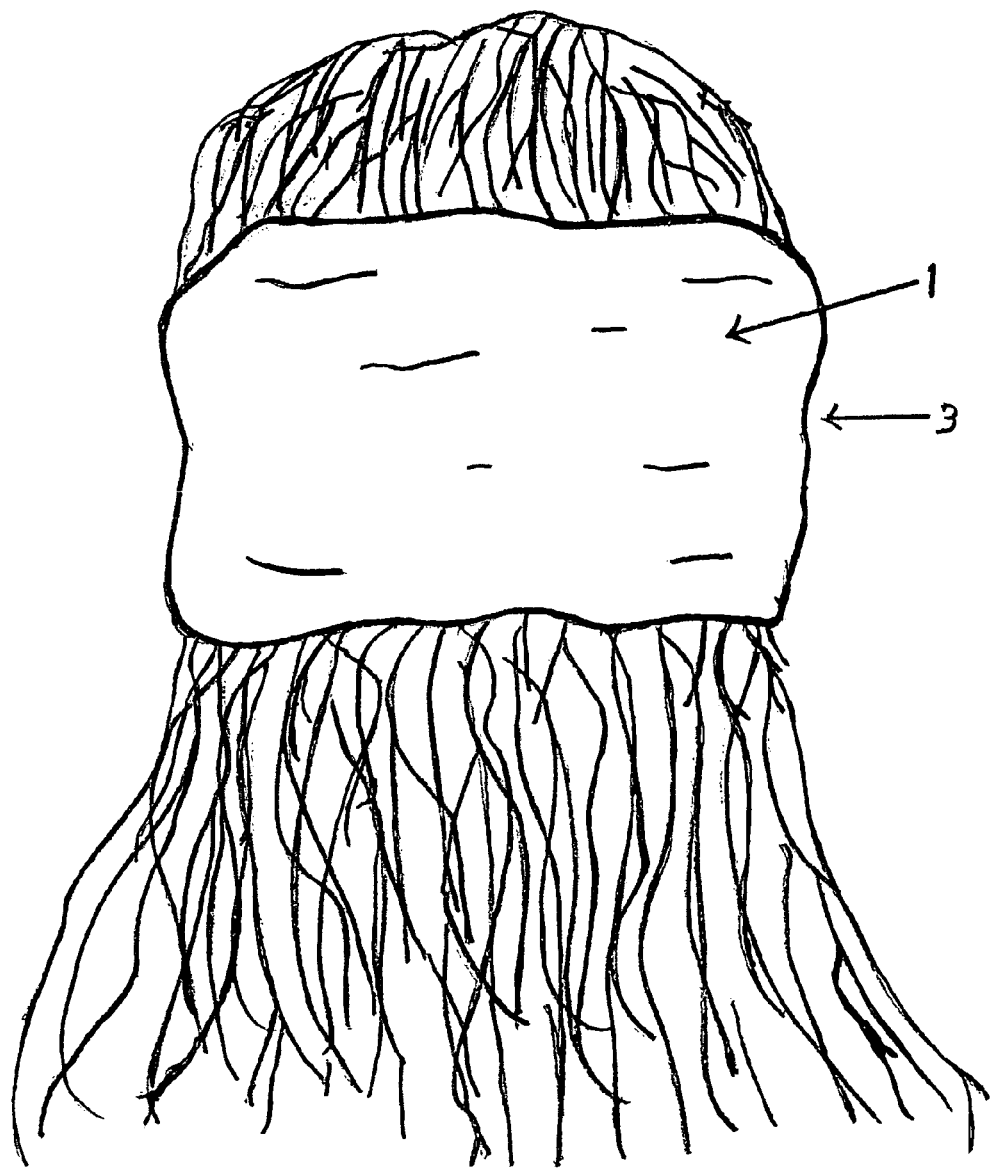
FIG. 10 illustrates a rear view of a person wearing the slip-over sleep mask of the present invention.

The slip-over sleep mask of the present invention 3 covers both ears of a person while being worn (See FIGS. 8-10.) Because of this, any noise levels, that surround a person, are reduced which would aid in helping a person sleep. Also, since the sleep mask of the present invention 3 is slipped-over a person's head as one piece, the natural stretch and cling fit that the sleep mask 3 exhibits helps to lightly compress the hair on a person's head, thus keeping it in a more conformed and organized shape. (See FIGS. 8-10.) This would be helpful if the hair on a person's head is too frizzy, unruly or in a state of experiencing too much volume.

All the above features can be achieved simultaneously while a person wears the slip-over sleep mask of the present invention 3 while sleeping.

The present invention may be embodied in other specific forms without deviating from the spirit or essential characteristics thereof and accordingly, reference should be made within the scope of the following claims, rather than to the foregoing specification.

I claim:

1. A slip-over light blocking sleep mask comprising:
   a cylindrically shaped body having a circumference and comprised of a soft flexible material, said body having an inside surface, an outside surface, an upper edge, a lower edge, a front and a back; said upper edge and said lower edge defining a height; said body being of substantially the same height throughout its circumference; said body being of sufficient height and of sufficient diameter to fit around a person's head and to cover the person's eyes and at least a substantial portion of said person's nose, and
   a separate first piece of ruffled or pleated material secured to the inside surface of the front of said body adjacent the lower edge thereof, said separate first piece of material extending downwardly below said lower edge;
   a separate second piece of ruffled or pleated material secured to the inside surface of the front of said body adjacent the lower edge thereof, said separate second piece of material extending downwardly below said lower edge, said first and second pieces of material being spaced apart from each other so as to be located beneath the person's eyes when said mask is worn; wherein each of said first and second pieces of material includes a vertical section and a horizontal section wherein said vertical section and said horizontal section are substantially perpendicular to one another and wherein said first and second pieces of material oppose one another.

2. The slip-over light blocking sleep mask as claimed in claim 1 wherein said vertical sections are substantially parallel to each other but spaced apart so as to be adapted to lie on either side of the person's nose when said mask is worn.

3. The slip-over light blocking sleep mask as claimed in claim 2 wherein said horizontal sections connect with their respective vertical sections and extend away from each other thereby being adapted to leave a space beneath the person's nose where there is no ruffled or pleated material.

* * * * *